Figure 1:
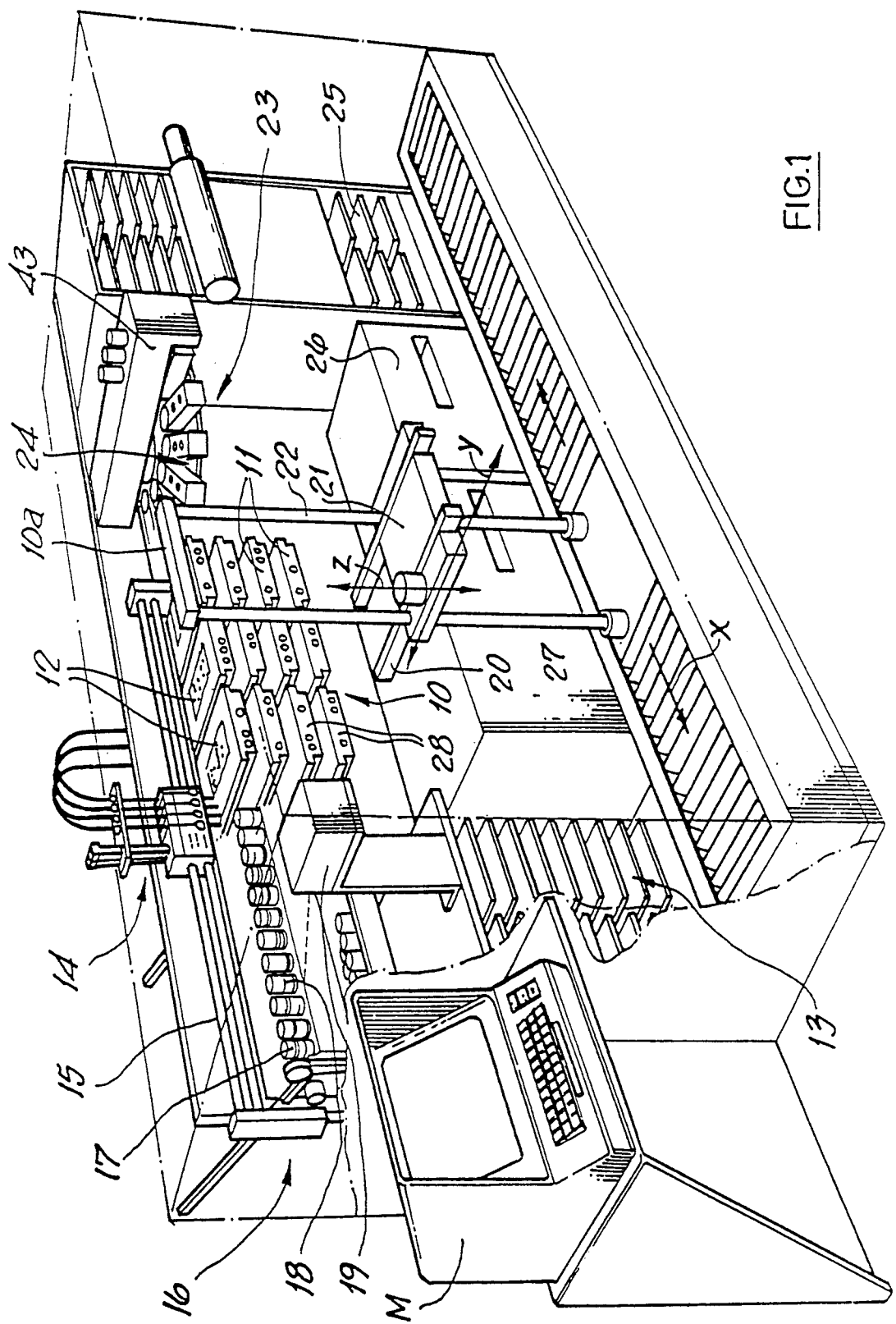

United States Patent

McCulloch et al.

[11] Patent Number: 5,122,342
[45] Date of Patent: Jun. 16, 1992

[54] BIO-FLUID ASSAY APPARATUS

[75] Inventors: Peter F. McCulloch, Wilmslow; Robert J. F. Moore, Stockport, both of England

[73] Assignee: Quatro Biosystems Limited, Manchester, England

[21] Appl. No.: 378,968

[22] Filed: Jul. 12, 1989

[30] Foreign Application Priority Data

Jul. 16, 1988 [GB] United Kingdom ............ 8816982.6

[51] Int. Cl.⁵ ............................................. G01N 35/04
[52] U.S. Cl. ........................................ 422/65; 422/67;
364/497; 436/47; 436/48; 436/808
[58] Field of Search ..................... 422/65, 67, 63;
364/497; 436/47, 48, 808

[56] References Cited

U.S. PATENT DOCUMENTS

| | | | |
|---|---|---|---|
| 3,917,455 | 11/1975 | Bak et al. | 422/67 |
| 4,279,861 | 7/1981 | Jessop | 364/497 |
| 4,582,990 | 4/1986 | Stevens | 422/65 |
| 4,676,951 | 6/1987 | Armes et al. | 422/65 |
| 4,720,463 | 1/1988 | Farber et al. | 422/65 |
| 4,727,033 | 2/1988 | Hijikata et al. | 422/65 |
| 4,751,184 | 6/1988 | Higo et al. | 422/65 |
| 4,812,392 | 3/1989 | Miyake et al. | 422/65 |
| 4,849,176 | 7/1989 | Sakagami | 422/65 |
| 4,952,518 | 8/1990 | Johnson et al. | 422/65 |

Primary Examiner—Lynn Kummert
Attorney, Agent, or Firm—Watts, Hoffmann, Fisher & Heinke

[57] ABSTRACT

There is disclosed micro-processor controlled bio-fluid assay apparatus wherein microtitre plates are on carriers having machine readable labels and wherein the samples of bio-fluid and reagent dispensers also preferably carry machine readable labels whereby the microprocessors which controls movement of the plates through the apparatus can verify correct operation thereof. Movement of the plates is effected by a plate carrier transfer mechanism which has the ability to move the plate carriers in any order and in either direction along each of the x, y and z axes.

12 Claims, 2 Drawing Sheets

BIO-FLUID ASSAY APPARATUS

This invention relates to bio-fluid assay apparatus of the kind (hereinafter termed of the kind referred to) wherein measured samples of bio-fluid, for example serum, are introduced into the wells of a microtitre plate (hereinafter 'plate') for subsequent chemical reaction and analysis.

A principal use of apparatus of the kind referred to is the carrying out of immuno-assay tests of serum, the wells of the plates being dosed with antibodies appropriate to the tests to be performed, suitable chemical reagents then being added prior to incubation washing and reading.

It is an object of the present invention to automate the operation of apparatus of the kind referred whilst ensuring a high level of security against error.

According to the present invention there is provided a bio-fluid assay apparatus of the kind wherein measured samples of bio-fluid, for example serum, are introduced into the wells of a microtitre plate for subsequent chemical reaction and analysis, comprising:

a micro-processor controller which may be input with details of patients and the tests required;

a plurality of discrete plate carriers;

an input magazine for said carriers;

an output magazine for said carriers;

a number of operational stations intermediate said input magazine and said output magazine;

plate carrier transport means which is controlled by the micro-processor for collecting plate carriers from the input magazine and progressing them through the successive operational stations and delivering them to the output magazine;

each plate carrier having a uniquely indentifying machine readable label which by reference to the data held by the micro-processor will indicate the particular type of the assay to be effected on the samples carried by the plate; and the transport means including means for reading said labels whereby the micro-processor control means can verify that each carrier taken from the input magazine was loaded and is selected correctly and can confirm the validity of other movements during the assay cycle.

A first operational station may be a transfer station at which the plates receive measured samples of bio-fluid transferred from a sample receiving section by an automatic pipette arrangement.

The sample receiving section may include a reader for machine readable labels on sample tubes to confirm that such are correctly loaded into the sample receiving section.

Other operational stations may include a station where chemical reagents are added to the plates by a reagent dispensing arrangement, a multiplate incubator, a plate washer and a plate reader. The incubator may be of the shaking kind.

The reagent dispensing arrangement may comprise an indexable dispensing head.

The head may comprise a plurality of reagent dispensers, which may be automatic pipettes, any one of which may be indexed to a dispensing position.

The pipettes may have multiple reagent exits.

The dispensing arrangement may further comprise a machine readable label associated with each reagent dispenser and indicating the identity of the reagents carried thereby and a label reader at the dispensing position.

The reagent dispensers may be operated by a simple set of powered piston plungers at the dispensing position.

The invention will be further apparent from the following description with reference to the figures of the accompanying drawings, which show, by way of example only, one form of bio-fluid assay apparatus embodying same.

Of the drawings

Figure 2:
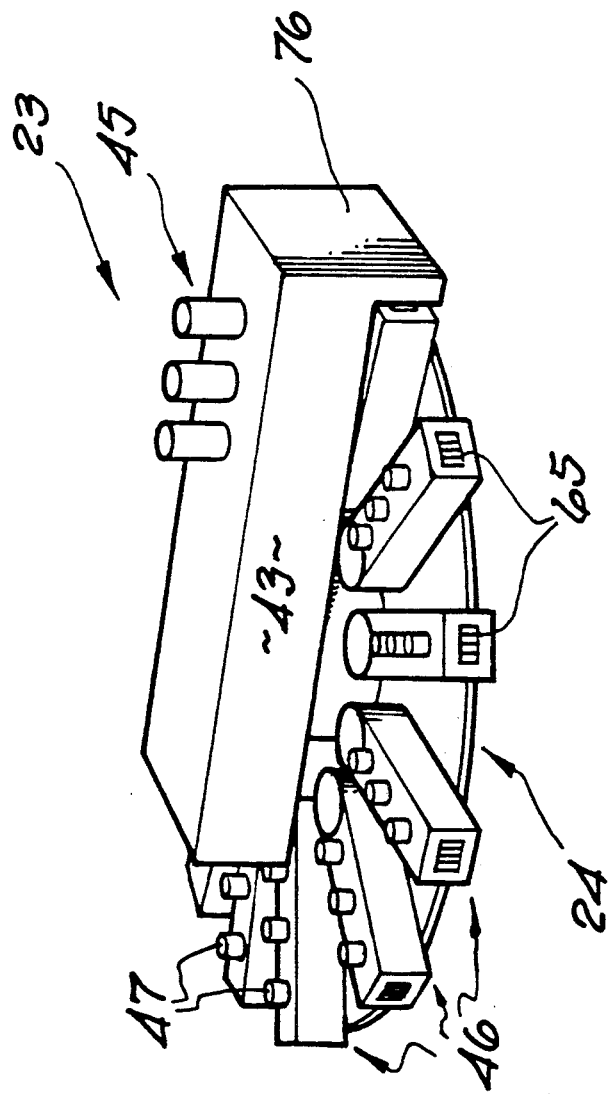

FIG. 1 shows a perspective diagrammatic view of the bio-fluid assay apparatus according to the invention; and FIG. 2 shows a detail of the reagent dispensing station of the apparatus of FIG. 1.

The apparatus is controlled by a suitably programmed micro-processor M, which is input with details of patients and the tests required for example Thyroid, Fertility, Steroid, HIV, Hepatitis and so on. Each test may require a plurality of separate assays. An operator will be directed by the micro-processor to load the apparatus with appropriate plates and samples of the patients' bio-fluids on specified carriers at specified locations. Thereafter the transfer of bio-fluid to the plates and progress of the plates through the various operational stations is under the control of the micro-processor which will give a print-out of all completed test results. In general the micro-processor will determine the order in which different assays will be performed to optimize throughput having regard to different residence time requirements at different operational stations for the different assays and other factors.

Turning now to FIG. 1, it will be seen that the apparatus has an input magazine generally indicated at 10 for plate carriers 11 each loaded with a microtitre plate 12, and an output magazine 13 which receives the carriers 11 after they have passed through the various operational stations of the apparatus.

The uppermost tier 10a of the input magazine 10 defines a transfer station at which the wells of the plates are dosed with measured volumes of bio-fluid transferred thereto by a multi-head automatic pipette arrangement generally indicated at 14 and indexable along the x-axis on rails 15 between the transfer station and a sample receiving section 16 loaded with tubes 17 of sample. The arrangement 14 is also indexable along the y-axis so that the pipette tips can register with any desired wells in a plate located on a carrier at the transfer station. The pipette tips are themselves movable along the z-axis as is obviously necessary for collection and delivery of sample. The pipette tips may be automatically exchanged or washed after each use in known manner. The tubes 17 carry bar-coded labels 18 (preferably printed under control of the micro-processor at the time of data input). A laser bar-code reader 19 which reports to the micro-processor M is provided to verify that the operator has positioned the sample tubes 17 in the receiving section at the locations directed.

Essentially the apparatus includes a plate carrier transfer mechanism comprising a fork 20 advanceable and retractable along the y-axis to engage with the underside of or be withdrawn from beneath a selected plate carrier. The fork 20 moves along the y-axis relative to a support 21 movable upwardly and downwardly along the z-axis relative to a support pillar 22 itself movable from side to side along the x-axis.

In accordance with the invention each of the plate carriers 11 carries a uniquely identifying machine readable label 28 which by reference to the data held by the micro-processor M will indicate the particular type of assay which the plate carried thereby is to undergo. The support 21 carries a reader for the labels 28 and this reader reports to the micro-processor on the identity of each carrier 11 which the fork 20 engages.

In this way the micro-processor can verify that the operator has positioned plate carriers 11 loaded with plates as directed and confirm the validity of other movements during the assay cycle.

Movement of the fork 20 along all three axes is under the control of the micro-processor to collect plate carriers from the input magazine 10 and position them in the transfer station and after they have been dosed with sample move them to a station generally indicated at 23 where reagents appropriate for the assays to be effected are dispensed into the wells of the plates from a rotatably indexable dispensing head 24.

The station 23, shown in more detail in FIG. 2, comprises an indexable dispensing head 24 rotatably mounted below a stationary module 43. The head 24 is indexed by commands from the micro-processor M. The head 24 comprises a plurality of arms 46 radially extending from its centre of rotation, each arm having a machine readable label 65 located on the face of the distal end thereof, said label 65 being indicative of the reagent carried. The label 65 is read by a label reader 76 attached to the module 43, which reports to the micro-processor M, enabling verification that the correct reagents are dispensed to the correct wells of each plate presented at the station 23.

Each of the arms 46 comprises a plurality of reagent dispensers in the form of multi-channel pipettes 47. The pipettes 47 are filled from containers of stock reagents' which may be located in the arms 46. Preferably three pipettes each possessing four reagent exit channels are located in each of the arms 46.

The module 43 has a plurality of powered piston plungers 45 located therein and extensible therethrough to engage with the pipettes 47. The plungers 45 are actuated, as directed by the micro-processor after verification of the labels 65 to operate the pipettes 47.

Whilst the reagents are being dispensed the plate carriers remain supported by the fork which executes necessary step movements in the x and y directions.

The fork 20 then moves the plate carrier into an incubator 25 and deposits it for the required residence time before collecting it for transfer to a washer 26 and reader 27 in turn. The incubator may have a variable heat control and may include a refrigerated zone, since it may be desired to carry out the colourmetric stage of some assays, for example the peroxidase catalysed cleavage of 3,3',5,5'-Tetramethylbenzidine Dihydrochloride, at temperatures below room temperature.

The plate carriers may remain supported by the fork whilst in the washer and reader and the fork may execute necessary step movements to enable reading of all wells. Alternatively the plate carriers may be deposited in the washer for a required time and also in the reader if of suitable design. After each plate has been read, the fork 20 transfers it to the output magazine 13 wherefrom it may be retrieved by the operator to enable the used plate to be discarded (or re-read for quality control purposes, for example) a new plate mounted and the carrier repositioned in the input magazine as directed.

The plates engage with the plate carriers such that their position thereon is precisely determined. Equally the plate carriers have projections or grooves which are engageable with complementary formations on the fork and the surfaces which support them at the various operational stations.

The labels 28 and 65 are conveniently magnetically coded and readable by an array of magnetically operable reed switches, but other kinds of label such as bar-coded labels are possible.

Apparatus, according to the invention, may be used, in addition to immuno-assay, in for example, an assay for the cell proliferative potential of bio-fluid. Cells may be seeded in the wells of the microtitre plates and cell growth or proliferation, for example, can be monitored spectrophotometrically after suitable cell staining and washing regimes. In this way, the vaso-proliferative potential of diabetic serum, for example, may be assessed.

It will be appreciated that it is not intended to limit the invention to the above example only, many variations, such as might readily occur to one skilled in the art, being possible, without departing from the scope thereof as defined by the appended claims.

We claim
1. A bio-fluid assay apparatus wherein measured samples of bio-fluid in the wells of a microtitre plate are analyzed comprising:
 a micro-processor controller which may be input with data including details of patients and different assays required;
 a plurality of discrete plate carriers;
 a magazine for said plurality of carriers;
 a plurality of operation stations including:
  a reagent dispensing station for adding chemical reagents to the plates by a reagent dispensing arrangement;
  a plate washing station;
  a plate reading station;
  plate carrier transport means constructed and arranged to move any plate carrier in either direction along each of x, y and z axes and which is controlled by the micro-processor controller for collecting plate carriers from said magazine and advancing the carriers as required through the plurality of operation stations;
 each plate carrier having a uniquely identifying machine readable label which by reference to the data held by the micro-processor controller will indicate the particular type of assay to be effected on the samples carried by each plate;
 the transport means including means for reading each label whereby the micro-processor controller can verify that each carrier taken from the magazine is loaded and is selected correctly and can confirm the validity of other movements of each carrier during each assay cycle; and
 the micro-processor controller being programmed to determine the order in which different assays are performed.

2. Apparatus according to claim 1, further including a transfer station at which each plate receives measured samples of bio-fluid transferred from a sample receiving section by an automatic pipette arrangement.

3. Apparatus according to claim 2, further comprising an incubator station.

4. Apparatus according to claim 2, wherein the sample receiving section includes a reader for machine readable labels on sample tubes to confirm that such are correctly loaded into the sample receiving section.

5. Apparatus according to claim 4, further comprising an incubator station.

6. Apparatus according to claim 1, wherein said reagent dispensing arrangement comprises an indexable dispensing head comprising a plurality of reagent dispensers.

7. Apparatus according to claim 6, in which the plurality of reagent dispensers are automatic pipettes, any one of which may be indexed to a dispensing position.

8. Apparatus according to claim 6, in which the dispensing arrangement further comprises machine readable labels indicating the identity of the reagents carried by each reagent dispenser, and a label reader at a dispensing position to verify that correct reagents are dispensed to correct plates.

9. Apparatus according to claim 8, in which powered piston plungers at the dispensing position operate the plurality of reagent dispensers.

10. Apparatus according to claim 1, further comprising a multiplate incubator.

11. Apparatus according to claim 1 further comprising a plate washer.

12. Apparatus according to claim 1, further comprising an incubator station.

* * * * *